United States Patent
Altschul et al.

(10) Patent No.: US 8,889,427 B2
(45) Date of Patent: Nov. 18, 2014

(54) DIAGNOSTIC DEVICE

(75) Inventors: Randice Lisa Altschul, Cliffside Park, NJ (US); Neil David Theise, New York, NY (US); Myron Rapkin, Indianapolis, IN (US); Rebecca O'Brien, Shell Knob, MO (US)

(73) Assignee: Pop Test, LLC, Cliffside Park, NJ (US)

( * ) Notice: Subject to any disclaimer, the term of this patent is extended or adjusted under 35 U.S.C. 154(b) by 0 days.

(21) Appl. No.: 13/463,956

(22) Filed: May 4, 2012

(65) Prior Publication Data

US 2012/0282636 A1   Nov. 8, 2012

Related U.S. Application Data

(60) Provisional application No. 61/518,344, filed on May 4, 2011.

(51) Int. Cl.
G01N 33/558 (2006.01)
G01N 21/64 (2006.01)
G01N 33/52 (2006.01)
G01N 21/84 (2006.01)

(52) U.S. Cl.
CPC .......... *G01N 21/6486* (2013.01); *G01N 33/525* (2013.01); *G01N 33/558* (2013.01); *G01N 21/8483* (2013.01); *G01N 2021/8494* (2013.01)
USPC ........................................................ 436/514

(58) Field of Classification Search
CPC .................................................... G01N 33/525
USPC ........................................................ 436/514
See application file for complete search history.

(56) References Cited

U.S. PATENT DOCUMENTS

| 4,493,795 A | | 1/1985 | Nestor et al. |
| 4,816,567 A | | 3/1989 | Cabilly et al. |
| 5,580,794 A | * | 12/1996 | Allen .............................. 436/169 |
| 5,872,713 A | * | 2/1999 | Douglas et al. ................. 702/85 |
| 5,965,848 A | | 10/1999 | Altschul |
| 6,124,585 A | | 9/2000 | Riedel et al. |

(Continued)

FOREIGN PATENT DOCUMENTS

| EP | 1043336 A2 | 11/2000 |
| RU | 2413947 C2 | 6/2009 |
| WO | 0142787 A2 | 6/2001 |

OTHER PUBLICATIONS

Deluca, et al. "Immunofluorescence Analysis" in antibody as a Tool, Marchalonism et al. eds. John Wiley & Sons, ltd. pp. 189-231 (1982).

(Continued)

*Primary Examiner* — Bao Thuy L Nguyen
*Assistant Examiner* — Gary E Hollinden
(74) *Attorney, Agent, or Firm* — Arthur Jacob

(57) ABSTRACT

The invention provides for rapid response analysis through lateral flow chromatographic assays of specific antigens present in human or animal fluids, or in agricultural, microbial or biological products, with an audio and visual result of the analysis and when needed, an electronic surge to provide heat for rapid results. A lateral flow device for conducting the analysis includes a plurality of components, and a method for making the device forms components of the device on an elongate, ribbon-like substrate of dielectric material, then folds the substrate into shorter lengths which are then secured together to establish a multiple-layered, self-sustaining structure.

5 Claims, 3 Drawing Sheets

(56) References Cited

U.S. PATENT DOCUMENTS

| | | | |
|---|---|---|---|
| 6,180,370 B1 | 1/2001 | Queen et al. | |
| 6,372,516 B1 | 4/2002 | Sun | |
| 6,528,325 B1 | 3/2003 | Hubscher et al. | |
| 6,670,115 B1 * | 12/2003 | Zhang | 435/5 |
| 7,148,424 B1 | 12/2006 | Altschul et al. | |
| 8,147,426 B2 * | 4/2012 | Neel et al. | 600/584 |
| 8,491,851 B2 * | 7/2013 | Baugh et al. | 422/402 |
| 2003/0219357 A1 * | 11/2003 | Douglas et al. | 422/58 |
| 2004/0234415 A9 * | 11/2004 | Douglas et al. | 422/58 |
| 2007/0087451 A1 | 4/2007 | Kirkegaard | |
| 2007/0117171 A1 * | 5/2007 | Wegner et al. | 435/14 |
| 2009/0155921 A1 | 6/2009 | Lu et al. | |
| 2011/0111517 A1 * | 5/2011 | Siegel et al. | 436/164 |
| 2012/0045845 A1 * | 2/2012 | Groll et al. | 436/150 |
| 2013/0065321 A1 * | 3/2013 | Nazareth et al. | 436/500 |

OTHER PUBLICATIONS

Galfre, et al., Meth Enzymol, 73:3-46 (1981).

Aurameas, et al. Scand. J. Immunol. vol. 8 Suppl. 7:7-23.

Rodwell, et al. Biotech., 3:889-894(1984).

Burns,, ed., Immunochemical Protocols, 3rd ed Humana Press (2005) pp. 27, 28, 41, 42, 71, 72, 97, 98, 123, 124, 127, 128, 135, 136, 207, 208, 209.

Sun Xiulan, et al Preparation of Gold Labeled Antibody Probe and its use in Immunochromatography Assay for detection of aflatoxim B1, Internatioanl Journal of Food Microbiology 99 (2005) 185-194.

J.K.Lee, et al. J. Agric Food Chem. 2003, 51, 3695-3703.

J.F. Lawrence, et al., J. Chromatography (1996) 732, 277-281.

J.F. Lawrence, et al. J. Chromatography (1996) 752-147-154.

* cited by examiner

DIAGNOSTIC DEVICE

This application claims benefit under 35 U.S.C. §119(e) to U.S. Provisional Patent Application 61/518,344 filed May 4, 2011, the disclosure of which is incorporated herein in its entirety.

BACKGROUND OF THE INVENTION

1. Field of Invention

This invention relates to a lateral flow strip assay system and uses thereof. In particular, the present invention relates to lateral flow assay systems for the simple and inexpensive detection of biomolecules.

2. Description of Related Art

The invention provides for rapid response immunoassay testing through lateral flow immunochromatographic assays of a specific antigen that is present in human or animal fluids with an audio and visual result of the test and when needed, an electronic surge to provide heat for rapid results. The present invention can be adapted for an ever growing range of tests for the clinical, veterinary, agricultural, food industry, bio-defense and environmental applications. Fluids include, but are not limited to, aqueous and/or solvent extraction solutions and/or suspensions, enrichment media, saliva, urine, blood and sweat.

The invention provides for a digital reader that provides the user with both a visual and an audio result. An example of this would be the determination of pregnancy. The pregnancy device would include conventional sensors to provide the user with a color band that appears or is absent when a specific antigen is present in a human fluid such as detecting chorionic gonadotropin (hCG) in urine. The speed of result can be increased with the electronic surge generated by a battery driven circuit to the sample. The result can then be visually read and/or revealed through audio means whereby the unit announces "Congratulations You Are Pregnant" or "I'm sorry you are not pregnant, better luck next time". The result can also be coupled with a fluorescent dye conjugate and read on a fluorescence reader. A device coupling lateral flow with the sensitivity of fluorescence would exhibit increased sensitivity.

The manufacture of the present invention can include, but is not limited to, plastic components, or as a continuous substrate as described in the embodiments of U.S. Pat. No. 5,965,848.

The present invention provides for a unique and novel, inexpensive, user friendly, optionally, disposable and/or recyclable, device for an already proven technology of lateral flow with the added aspect of electronic surge to provide the sample with a rapid test result that be can heard as well as seen.

Current lateral flow devices often require use of an incubator, or other extrinsic heating device, in order to get an accurate result. One exemplary advantage of the device of the invention is that the heating element is, for example, built in to the device. In one embodiment, the device of the invention is thus portable, and no extrinsic heating is necessary.

The invention can be produced to test for a variety of biological elements including but not limited to: infections diseases, such as influenza, strep, HIV, measles, rotavirus, typhoid, hepatitis; drugs of abuse, such as cocaine, heroin, pain killers, cocaine, methamphetamine and other drugs; hormones such as HcG, estrogen, cortisol; clinical indications, such as pregnancy, prostatic acid phosphatase, various tumor markers, cholesterol, glucose, and cancer markers; therapeutic drug monitoring of drugs such as, theophylline, aminoglycoside antibiotics (gentamicin), antiepileptics (such as carbamazepine, phenyloin, and valproic acid), mood stabilizers, especially lithium citrate, antipsychotics (such as pimozide and clozapine). The device of the invention may comprise, for example, temperature control and/or on-board mixing as an aid in viscosity control of the reaction, to ensure better accuracy and precision.

All references cited herein are incorporated herein by reference in their entireties.

BRIEF SUMMARY OF THE INVENTION

The invention provides a lateral flow device for qualitative or quantitative analysis of a target analyte in a sample, comprising: a) an absorbent sample pad onto which the sample is applied; b) a conjugate or agent pad comprising at least one specific binding agent specific to the target analyte, and optionally conjugated to a signal-generating agent; c) a reaction membrane onto which at least one capture agent is immobilized in a line across the membrane as a capture zone or test line, further optionally comprising a control zone, containing a binding agent specific for the capture agent; and d) a wick or waste reservoir, which draws the sample across the reaction membrane and collects it; e) at least one circuit to provide an electronic surge to the sample; f) an electric current source; and g) a means to indicate the results. The invention further provides a device of the invention wherein the electric current source is a battery. The invention further provides a device of the invention, wherein the electronic surge is a battery driven circuit. The invention further provides a device of the invention wherein the results of the analysis are increased by the electronic surge to the sample. The invention further provides a device of the invention wherein the results of the analysis are increased with the electronic surge generated by a battery driven circuit to the sample to provide heat. The invention further provides a device of the invention wherein the electric current source is connected to a conductive material for inducing resistive heating therein. The invention further provides a device of the invention wherein the device includes a digital reader that provides a user with both a visual and audio result. The invention further provides a device of the invention, wherein the means to indicate the result is selected from the group consisting of visual means, audio means, and combinations thereof. The invention further provides a device of the invention wherein the signal generating agent is a fluorescent dye which forms a conjugate with the specific binding agent and read on a fluorescence reader. The invention further provides a device of the invention wherein the signal generating agent is selected from the group consisting of chromogens, enzymes, catalysts, fluorescent compounds, chemiluminescent compounds, fluorescein, rhodamine, radioactive labels, magnetic beads or magnetic particles, enzymes or substrates, dioxetanes, acridiniums, phenanthridiniums, luminol, alkaline phosphatase, horseradish peroxidase, beta-galactosidase, radioactive elements, direct visual labels, vesicles containing signal producing substances, colorimetric labels, direct visual labels, colloidal metallic and metallic and non-metallic colored particles, dye particles, organic polymer latex colored particles, and combinations thereof.

The invention further provides a device of the invention wherein the specific binding agent is selected from the group consisting of hapten-anti-hapten systems, biotin and anti-biotin, avidin or biotin, a carbohydrate, a lectin, a complementary nucleotide sequence, an effector or a receptor molecule, an enzyme cofactor and an enzyme, an enzyme inhibitor or an enzyme, and combinations thereof.

The invention further provides a device of the invention wherein the specific binding agent is selected from a group consisting of an antibody, an antigen, a nucleic acid aptamer, a hapten, an antigenic protein, DNA, DNA-binding protein, a hormone-receptor, and combinations thereof.

The invention further provides a device of the invention wherein the specific binding agent is selected from the group consisting of antibody molecules, polyclonal antibodies, monoclonal antibodies, hybrid or chimeric antibody molecules, F(ab')2 fragments, F(ab) fragments; Fv molecules, single chain Fv molecules (sFv), humanized antibody molecules, any functional fragments of antibodies which retain immunological binding properties, and combinations thereof.

The invention further provides a device of the invention wherein the specific binding agent is specific for an analyte selected from the group consisting of hormones, pregnancy hormones, prostatic acid phosphatase, HIV, Rotavirus, Typhoid, cocaine, methamphetamine, drugs, hepatitis, tumor markers, cortisol, cholesterol, glucose, cancer markers, influenzas, and combinations thereof.

The invention further provides a device of the invention wherein the sample is selected from or is derived from the group comprising: agricultural product, microbial product, and biological product.

The invention further provides a device of the invention wherein the sample is an agricultural product selected from the group comprising a seed, grain, and plant extract.

The invention further provides a device of the invention wherein the sample contains particulate materials selected from the group comprising grain extract, cell extract and microbial extract.

The invention further provides a device of the invention wherein the specific binding agent is specific for an analyte selected from the group consisting of agriculture fungal antigens, agriculture viral infections, pesticide residues, genetically modified organisms (GMO), and genetically modified food.

The invention further provides a device of the invention wherein the specific binding agent is specific for an analyte selected from the group consisting of agrochemicals selected from the group consisting of herbicides, fungicides, insecticides plant growth regulators, agrochemicals, insecticides, and *Bacillus thurigiensis* derived proteins (Bt).

The invention further provides a device of the invention wherein the specific binding agent is specific for an agrochemical selected from the group consisting of organic molecules, inorganic molecules, proteins, polypeptides, and small organic molecules.

The invention further provides a device of the invention wherein the specific binding agent is specific for an analyte selected from the group consisting of food borne bacterial pathogens, bacterial and fungal toxins, mycotoxins, and bacterial isolates.

The invention further provides a device of the invention wherein the sample is a biological sample.

The invention further provides a device of the invention wherein the sample is selected from the group consisting of bodily fluids, blood products, plasma, serum, urine, semen, saliva, sputum, proteins, nucleic acids, carbohydrates, and combinations thereof.

The invention further provides a device of the invention wherein the signal generating agent is a fluorescent compound.

The invention further provides a device of the invention wherein the capture zone on the membrane comprises immobilized antigens.

The invention further provides a device of the invention wherein the capture zone on the membrane comprises enzymes.

The invention further provides a device of the invention wherein there is multiple capture zones to create a multiplex test.

The invention further provides a device of the invention wherein the analyte is selected from the group consisting of an antibody, an antigen, a nucleic acid aptamer, a hapten, a antigenic protein, DNA, DNA-binding protein, a hormone, a tumor-specific marker, a tissue-specific marker, and combinations thereof.

The invention provides a method for the manufacture of the device of the invention. The invention provides a method of detection of analyte in a sample, comprising application of a biological sample to the device of the invention.

The invention provides a lateral flow device for qualitative or quantitative analysis of a target analyte in a sample, which is a disposable portable electronic device having a body of prescribed length, width and thickness, a desired mechanical stiffness, and circuitry including conductors and components, comprising; an elongate, ribbon-like substrate of dielectric material, the substrate having a continuous length many times greater than the prescribed length of the body, a thickness many times less than the prescribed thickness of the body, and opposite faces; at least some of the conductors and some of the components being formed on the substrate, the formed conductors and components being formed on only one of the faces of the substrate and extending along a length of the substrate many times greater than the prescribed length of the body of the electronic device; the ribbon-like substrate of dielectric material having a high degree of flexibility such that at least the length of the substrate is folded tightly upon itself into at least several shorter lengths within the prescribed length of the body, with the at least several shorter lengths juxtaposed with one another for securement to one another over the shorter lengths within the prescribed thickness of the body and with the formed conductors and components including portions extending along each of at least several of the shorter lengths of the substrate so as to be juxtaposed with one another; the juxtaposed shorter lengths of the substrate being secured together along the juxtaposed shorter lengths to establish a multiple-layered self-sustaining structure having a high degree of stiffness, as compared to the flexibility of the ribbon-like substrate, which structure, in and of itself, forms the body of the device, with the juxtaposed portions of the formed conductors and components electrically insulated from one another within the structure and the high degree of stiffness of the structure providing the desired mechanical stiffness of the body; wherein the device further comprises: an absorbent sample pad onto which the sample is applied; a conjugate or agent pad comprising at least one specific binding agent specific to the target analyte, and optionally conjugated to a signal-generating agent; a reaction membrane onto which at least one capture agent is immobilized in a line across the membrane as a capture zone or test line, further optionally comprising a control zone, containing a binding agent specific for the capture agent; and a wick or waste reservoir, which draws the sample across the reaction membrane and collects it; at least one circuit to provide an electronic surge to the sample; an electric current source; and a means to indicate the results. The invention further provides a device of the invention wherein the electric current source is a battery. The invention further provides a device of the invention wherein the electronic surge is a battery driven circuit. The invention further provides a device of the invention wherein the results of the analysis are increased by the electronic surge to the sample. The invention further provides a device of the invention wherein the results of the analysis are increased with the electronic surge generated by a battery driven circuit to the sample to provide heat. The invention further provides a device of the invention wherein the electric current source is connected to a conductive material for inducing resistive heating therein. The invention further provides a device of the invention wherein the device includes a digital reader that provides a user with both a visual and audio result. The invention further provides a device of the invention wherein the means to indicate the result is selected from the group consisting of visual means, audio means, and combinations thereof. The invention further provides a device of the invention wherein the substrate has a width corresponding to the prescribed width of the body. The invention further provides a device of the invention wherein the juxtaposed lengths of the substrate are laminated together. The invention further provides a device of the invention wherein the formed conductors and components are printed upon the one of the faces of the substrate. The invention further provides a device of the invention wherein the substrate is folded so as to be wound upon itself within the shorter lengths, with the one of the faces of the substrate confronting the other of the faces of the substrate along the shorter lengths and the material of the substrate electrically insulating the juxtaposed portions of the printed conductors and components from one another. The invention further provides a device of the invention including openings in the substrate, the openings being spaced from one another along the length of the substrate for registration with one another in the juxtaposed shorter lengths to establish at least one cavity in the folded substrate, and at least one of the components of the circuitry being located within the cavity. The invention further provides a device of the invention wherein others of the components of the circuitry are mounted externally upon the folded substrate. The invention further provides a device of the invention including an external sheath over the folded substrate.

The invention provides a method for making a lateral flow device for qualitative or quantitative analysis of a target analyte in a sample, wherein the device is a disposable portable electronic device having a body of prescribed length, width and thickness, a desired mechanical stiffness, and circuitry including conductors and components, the method comprising: forming at least some of the conductors and some of the components on an elongate, ribbon-like substrate of dielectric material, the ribbon-like substrate having a continuous length many times greater than the prescribed length of the body, a thickness many times less than the prescribed thickness of the body, opposite faces, and a high degree of flexibility, the formed conductors and components being formed on only one of the faces of the substrate and extending along a length of the substrate many times greater than the prescribed length of the body of the electronic device; folding the substrate tightly upon itself into at least several shorter lengths within the prescribed length of the body, with the at least several shorter lengths juxtaposed with one another for securement to one another over the shorter lengths within the prescribed thickness of the body and with the formed conductors and components including portions extending along each of at least several of the shorter lengths of the substrate so as to be juxtaposed with one another; and securing together the juxtaposed shorter lengths of the substrate along the juxtaposed shorter lengths to establish a multiple-layered self-sustaining structure having a high degree of stiffness, as compared to the flexibility of the ribbon-like substrate, which structure, in and of itself, forms the body of the device, with the juxtaposed portions of the formed conductors and components electrically insulated from one another within the structure and the high degree of stiffness of the structure providing the desired mechanical stiffness of the body, wherein the device further comprises: an absorbent sample pad onto which the sample is applied; a conjugate or agent pad comprising at least one specific binding agent specific to the target analyte, and optionally conjugated to a signal-generating agent; a reaction membrane onto which at least one capture agent is immobilized in a line across the membrane as a capture zone or test line, further optionally comprising a control zone, containing a binding agent specific for the capture agent; and a wick or waste reservoir, which draws the sample across the reaction membrane and collects it; at least one circuit to provide an electronic surge to the sample; an electric current source; and a means to indicate the results.

The invention further provides a method of the invention wherein the electric current source is a battery. The invention further provides a method of the invention wherein the electronic surge is a battery driven circuit. The invention further provides a method of the invention wherein the results of the analysis are increased by the electronic surge to the sample. The invention further provides a method of the invention wherein the results of the analysis are increased with the electronic surge generated by a battery driven circuit to the sample to provide heat. The invention further provides a method of the invention wherein the electric current source is connected to a conductive material for inducing resistive heating therein. The invention further provides a method of the invention wherein the device includes a digital reader that provides a user with both a visual and audio result. The invention further provides a method of the invention wherein the means to indicate the result is selected from the group consisting of visual means, audio means, and combinations thereof. The invention further provides a method of the invention wherein the juxtaposed lengths of the substrate are secured together by laminating the juxtaposed lengths together. The invention further provides a method of the invention wherein the formed conductors and components are formed by printing upon the one of the faces of the substrate. The invention further provides a method of the invention wherein the substrate is folded by being wound upon itself within the shorter lengths, with the one of the faces of the substrate confronting the other of the faces of the substrate along the shorter lengths and the material of the substrate electrically insulating the juxtaposed portions of the printed conductors and components from one another. The invention further provides a method of the invention including establishing openings in the substrate, with the openings spaced from one another along the length of the substrate so as to be registered with one another in the juxtaposed shorter lengths for establishing at least one cavity in the folded substrate, and placing at least one of the components of the circuitry within the cavity. The invention further provides a method of the invention wherein others of the components of the circuitry are mounted externally upon the folded substrate. The invention further provides a method of the invention including encasing the folded substrate within an external sheath.

The invention provides a lateral flow device for qualitative or quantitative analysis of a target analyte in a sample, which is a disposable electronic device having a body constructed of juxtaposed lengths of an elongate, ribbon-like substrate of dielectric material secured together to establish a multiple-layered self-sustaining structure, and circuitry formed on the substrate, comprising: at least a portion of the circuitry being constructed of a deconstructable material which deconstructs to render the device inoperative in response to reaching a predetermined accumulated amount of time during which the circuitry is operated, wherein the device further comprises: an absorbent sample pad onto which the sample is applied; a conjugate or agent pad comprising at least one specific binding agent specific to the target analyte, and optionally conjugated to a signal-generating agent; a reaction membrane onto which at least one capture agent is immobilized in a line across the membrane as a capture zone or test line, further optionally comprising a control zone, containing a binding agent specific for the capture agent; and a wick or waste reservoir, which draws the sample across the reaction membrane and collects it; at least one circuit to provide an electronic surge to the sample; an electric current source; and a means to indicate the results. The invention further provides a device of the invention wherein the electric current source is a battery. The invention further provides a device of the invention wherein the electronic surge is a battery driven circuit. The invention further provides a device of the invention wherein the results of the analysis are increased by the electronic surge to the sample. The invention further provides a device of the invention wherein the results of the analysis are increased with the electronic surge generated by a battery driven circuit to the sample to provide heat. The invention further provides a device of the invention wherein the electric current source is connected to a conductive material for inducing resistive heating therein. The invention further provides a device of the invention wherein the device includes a digital reader that provides a user with both a visual and audio result. The invention further provides a device of the invention wherein the means to indicate the result is selected from the group consisting of visual means, audio means, and combinations thereof. The invention further provides a device of the invention wherein the substrate comprises paper.

The invention provides a lateral flow device for qualitative or quantitative analysis of a target analyte in a sample, which is a disposable electronic device having a body constructed of juxtaposed lengths of an elongate, ribbon-like substrate of dielectric material secured together to establish a multiple-layered self-sustaining structure, and circuitry formed on the substrate, the improvement comprising: at least a portion of the circuitry being constructed of a deconstructable material which deconstructs to render the device inoperative in response to reaching a predetermined accumulated amount of time during which the circuitry is operated, the portion of the circuitry including at least one link constructed of a deconstructable material initially electrically conductive and rendered non-conductive in response to a prescribed current flow through the link over a predetermined accumulated amount of time, whereby the circuitry is deconstructed and the device is rendered inoperative upon reaching the predetermined accumulated amount of time wherein the device further comprises: an absorbent sample pad onto which the sample is applied; a conjugate or agent pad comprising at least one specific binding agent specific to the target analyte, and optionally conjugated to a signal-generating agent; a reaction membrane onto which at least one capture agent is immobilized in a line across the membrane as a capture zone or test line, further optionally comprising a control zone, containing a binding agent specific for the capture agent; and a wick or waste reservoir, which draws the sample across the reaction membrane and collects it; at least one circuit to provide an electronic surge to the sample; an electric current source; and a means to indicate the results. The invention further provides a device of the invention wherein the electric current source is a battery. The invention further provides a device of the invention wherein the electronic surge is a battery driven circuit. The invention further provides a device of the invention wherein the results of the analysis are increased by the electronic surge to the sample. The invention further provides a device of the invention wherein the results of the analysis are increased with the electronic surge generated by a battery driven circuit to the sample to provide heat. The invention further provides a device of the invention wherein the electric current source is connected to a conductive material for inducing resistive heating therein. The invention further provides a device of the invention wherein the device includes a digital reader that provides a user with both a visual and audio result. The invention further provides a device of the invention wherein the means to indicate the result is selected from the group consisting of visual means, audio means, and combinations thereof.

The invention provides a lateral flow device for qualitative or quantitative analysis of a target analyte in a sample, which is a disposable electronic device having a body constructed of juxtaposed lengths of an elongate, ribbon-like substrate of dielectric material secured together to establish a multiple-layered self-sustaining structure, and circuitry formed on the substrate, the improvement comprising: at least a portion of one of the substrate and the circuitry being constructed of a deconstructable material which deconstructs in response to exposure of the deconstructable material to at least one of ambient conditions including ambient air, ambient light and ambient moisture; and a sheath surrounding the multi-layered self-sustaining structure, the sheath being constructed of a material impervious to at least a corresponding one of ambient air, ambient light and ambient moisture wherein the device further comprises: an absorbent sample pad onto which the sample is applied; a conjugate or agent pad comprising at least one specific binding agent specific to the target analyte, and optionally conjugated to a signal-generating agent; a reaction membrane onto which at least one capture agent is immobilized in a line across the membrane as a capture zone or test line, further optionally comprising a control zone, containing a binding agent specific for the capture agent; and a wick or waste reservoir, which draws the sample across the reaction membrane and collects it; at least one circuit to provide an electronic surge to the sample; an electric current source; and a means to indicate the results. The invention further provides a device of the invention wherein the electric current source is a battery. The invention further provides a device of the invention wherein the electronic surge is a battery driven circuit. The invention further provides a device of the invention wherein the results of the analysis are increased by the electronic surge to the sample. The invention further provides a device of the invention wherein the results of the analysis are increased with the electronic surge generated by a battery driven circuit to the sample to provide heat. The invention further provides a device of the invention wherein the electric current source is connected to a conductive material for inducing resistive heating therein. The invention further provides a device of the invention wherein the device includes a digital reader that provides a user with both a visual and audio result. The invention further provides a device of the invention wherein the means to indicate the result is selected from the group consisting of visual means, audio means, and combinations thereof. The invention further provides a device of the invention wherein the sheath includes a selectively opened portion for selective exposure of the deconstructable material to the ambient conditions. The invention further provides a device of the invention wherein the substrate comprises paper.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
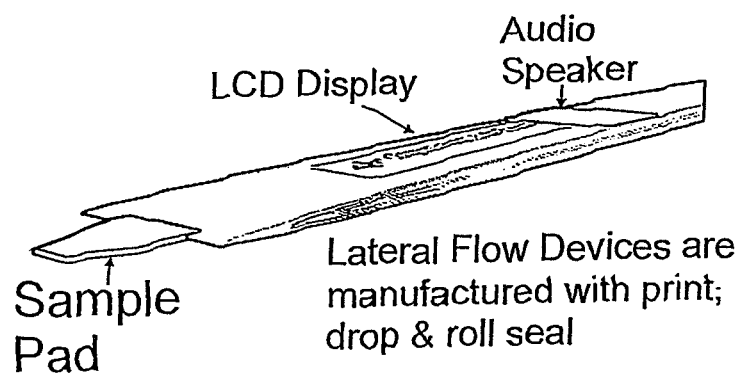
FIG. 1 is an example of a device of the invention which in this embodiment comprises a sample pad, an LCD display, and an audio speaker.
Figure 2:
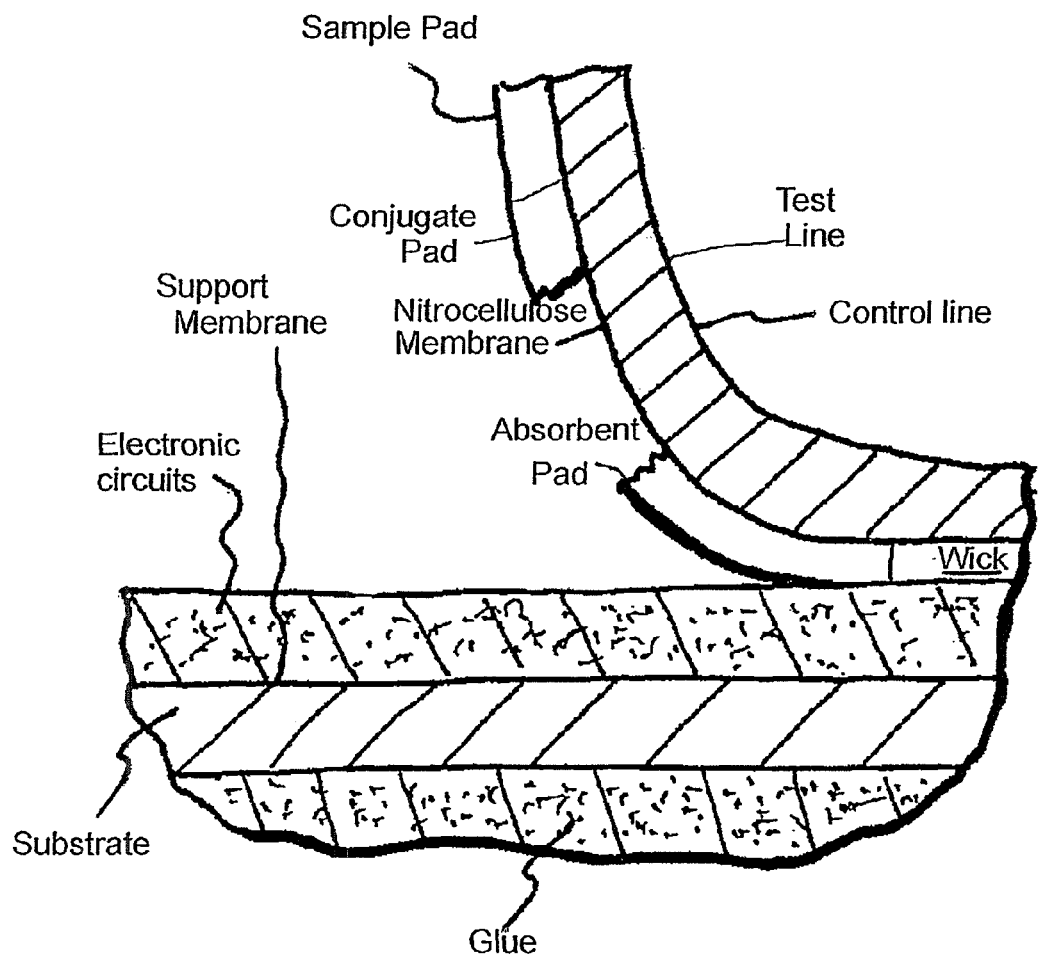
FIG. 2 is a cross-sectional view demonstrating a lateral flow device of the invention.
Figure 3:
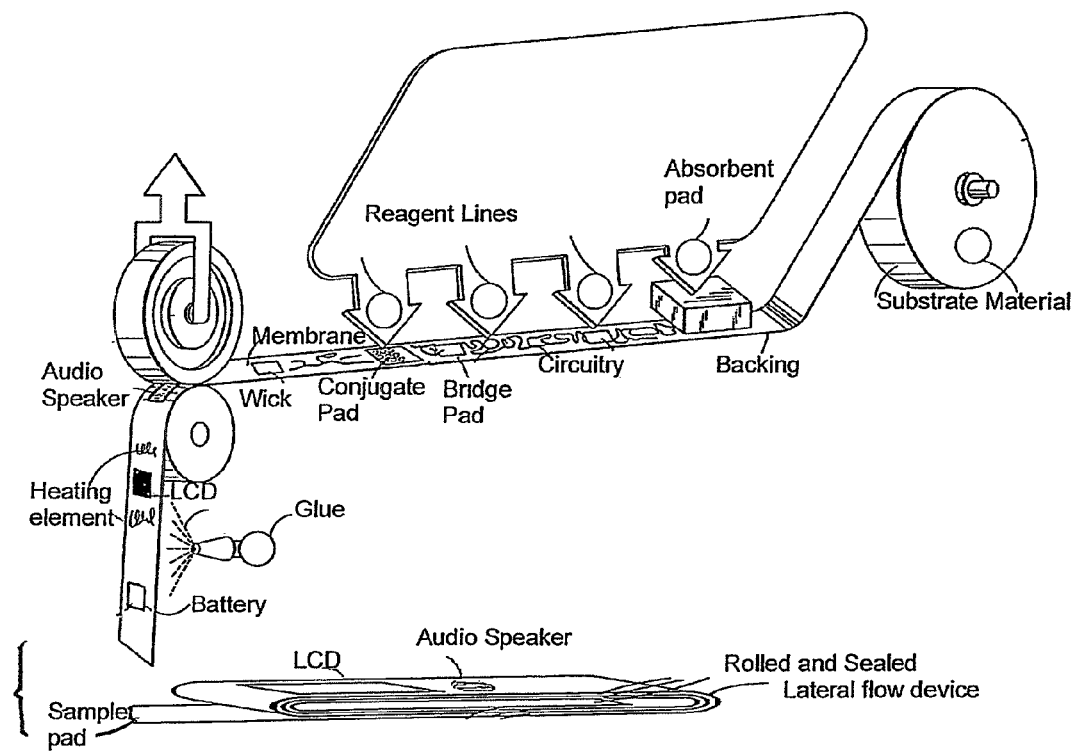
FIG. 3 is a diagrammatic illustration of successive portions of a process by which a lateral flow device of the invention can be manufactured.

Lateral-flow immunoassays, with their ease of use, speed and reliability, are widely used for self-testing and in the clinical setting. In the general method, a liquid sample suspected of containing the analyte is applied to a porous carrier. Different porous materials are commonly used for the porous carrier, and can differ in pore size, flow rate, protein-binding specifications and pre-treatment, etc. Essentially, all of the physical activities (e.g., liquid migration) and chemical reactions take place in the porous carrier, in the following order.

First, a liquid sample to be tested is introduced to a designated area in the sample pad. From this point forward, the liquid sample migrates within the porous carrier to the direction of the wick or waste reservoir end. At the outset of the migration, the liquid sample is frequently optimized for reaction by means of chemicals, e.g., pH agents or buffers, surfactants, and/or blockers impregnated into the porous carrier.

Second, while migrating in the porous carrier, the sample mobilizes a labeled reagent that has been reversibly (temporarily) immobilized in the porous carrier. The zone where the mobilizable labeled reagent is located is often referred to as the conjugate or reagent pad.

Third, while analyte is reacting with the mobilized labeled reagent, the liquid sample and mobilized labeled reagent migrates further within the porous carrier to the reaction or detection zone, where reagent that binds the same analyte is fixed or immobilized, for example, in the form of a line. When analyte is present in the liquid sample, a sandwich in the form of the mobilized labeled reagent:analyte:immobilized reagent is formed, and the resulting concentration of the labeled reagent leads to a visible line appearing in the reaction or detection zone, which is indicative of, for example, a positive result.

Lastly, remaining sample liquid, together with the rest of the labeled reagent may further migrate to a control zone, where a second line appears indicating that sample has progressed through the detection and control zones and that the assay has provided a valid test result. The rest of the sample and the remaining labeled reagent then migrate to a wick or waste reservoir. Labeled reagent remaining in the porous carrier (other than in the detection zone, control zone or wick) makes up any background signal. In some instances where the migration direction reverses, so called back flow, occurs. Furthermore, the porous carrier can be pre-treated with chemicals e.g. surfactants.

Lateral-flow immunoassays can also function on the basis of competitive binding of the analyte. In these devices, lack of the test line generally indicates a positive result.

An example of a lateral-flow immunoassay device is a pregnancy test. These devices are commonly provided for home use, in a plastic housing with a fibrous or a porous extension, which can be held to a urine stream to collect urine sample into the housing. The urine sample collected this way then migrates to the porous carrier, which contains the labeled reagent and the series of events mentioned above starts. The analyte detected in a pregnancy test may be human Chorionic Gonadotropin (hCG) and the reagents commonly used are anti-hCG monoclonal or polyclonal antibodies. The most common labels are gold or latex particles.

Another known example of a lateral-flow immunoassay device commonly provided for home use is an ovulation test, the analyte being Luteinizing Hormone (LH) and reagents being anti-LH, and the rest of the device being similar to a pregnancy test.

"Analyte," as used herein, is the substance to be detected which may be present in the test sample, including, biological molecules of interest, small or large molecules, in free suspension (e.g. hormones in urine, saliva, blood, plasma, serum, tissue aspirate) or still attached (on the surface or within) to biological agents (e.g. viruses, bacteria, fungi, cells that have been shed from tissues, or cells extracted from tissue or body cavities by biopsy, aspiration, or surgical procedure), within viruses or cells or on their surfaces and the like. The analyte can include a protein or glycoprotein, a polypeptide, an amino acid, a nucleotide target, an organic or inorganic chemical, a drug, a hormone, and the like.

A "specific binding agent," as used herein, may be, for example, a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding agents, for example, an analyte-analog. Immunoreactive specific binding agents include antigens, antigen fragments, antibodies and antibody fragments, both monoclonal and polyclonal and complexes thereof, including those formed by recombinant DNA molecules.

Specific binding agents may include an immunoreactive specific binding agent. As such, the term "specific binding agent" encompasses antibody molecules (obtained from both polyclonal and monoclonal preparations), as well as, the following: hybrid (chimeric) antibody molecules (see, for example, U.S. Pat. No. 4,816,567); F(ab')$_2$ and F(ab) fragments; Fv molecules (non-covalent heterodimers; single chain Fv molecules (sFv); humanized antibody molecules; and, any functional fragments obtained from such molecules, wherein such fragments retain immunological binding properties of the parent antibody molecule (see U.S. Pat. No. 6,180,370).

The term "hapten," as used herein, refers to a partial antigen or non-protein binding member which is capable of binding to an antibody, but which is not capable of eliciting antibody formation unless coupled to a carrier protein.

The term "lectin," as used herein, refers to a sugar-binding proteins (not to be confused with glycoproteins, which are proteins containing sugar chains or residues) that are highly specific for their sugar moieties. They play a role in biological recognition phenomena involving cells and proteins.

A "capture agent," as used herein, refers to an unlabeled specific binding agent that is specific either for the analyte as in a sandwich assay, for the indicator reagent or analyte as in a competitive assay, or for an ancillary specific binding agent, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator agent" comprises a "signal-generating compound" ("label") which is capable of generating and generates a measurable signal detectable by external means. In some embodiments, the indicator reagent is conjugated ("attached") to a specific binding agent. In addition to being an antibody member of a specific binding pair, the indicator reagent also can be a member of any specific binding pair, including either hapten-anti-hapten systems such as biotin or anti-biotin, avidin or biotin, a carbohydrate, or a lectin, a complementary nucleotide sequence, an effector or a receptor molecule, an enzyme cofactor and an enzyme, an enzyme inhibitor or an enzyme and the like. An immunoreactive specific binding agent can be an antibody, an antigen, or an antibody/antigen complex that is capable of binding either to the polypeptide of interest as in a sandwich assay, to the capture reagent as in a competitive assay, or to the ancillary specific binding agent as in an indirect assay. When describing probes and probe assays, the term "reporter molecule" may be used. A reporter molecule comprises a signal generating compound as described hereinabove conjugated to a specific binding agent of a specific binding pair.

The various "signal-generating agents" (e.g., labels) contemplated include chromagens, catalysts such as enzymes, luminescent compounds such as fluorescein and rhodamine, chemiluminescent compounds such as dioxetanes, acridiniums, phenanthridiniums, and luminol, radioactive elements and direct visual labels. Examples of enzymes include alkaline phosphatase, horseradish peroxidase, beta-galactosidase and the like. The selection of a particular label is not critical, but it should be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips or other lateral flow strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips, are all suitable examples. It is contemplated and within the scope of the present invention that the solid phase also can comprise any suitable porous material.

As used herein, the terms "detect", "detecting", or "detection" may describe either the general act of discovering or discerning or the specific observation of a detectably labeled composition.

As used herein, the term "sample" is used in its broadest sense. In one sense it can refer to a tissue sample. In another sense, it is meant to include a specimen or culture obtained from any source, as well as biological. In another sense, it is meant to refer to environmental samples. Biological samples may be obtained from animals (including humans) or from plants and encompass fluids, solids, tissues, and gases. Biological samples include, but are not limited to bodily fluids such as blood products, such as plasma, serum and the like, urine, semen, saliva, sputum and fractions thereof; proteins, glycoproteins, nucleic acids, hormones, antibodies etc. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

Lateral Flow

The methods of the invention may be carried out using, for example, a lateral flow assay. Such lateral flow assays have the potential to be a cost-effective, fast, simple, and sensitive method, for instance for on-site screening assays. The lateral flow assay comprises a carrier that allows a lateral flow to occur wherein either the sample or the detection reagent is displaced from one location on the carrier to another. There are many formats of lateral flow assays suitable for use in a method embodied by the invention, and the skilled person will readily know how to select and optimize a particular format.

Lateral flow type test strips are an example of a test utilizing a solid support to capture a detectable signal. The test consists of three overlapping membranes that are laid down onto a backing card such that they slightly overlap each other. The first membrane known as the sample pad is usually a glass fiber membrane where the sample is introduced to the test strip. The second membrane is the capture membrane whereupon a capture antibody specific to the target of interest is striped (deposited) onto and is known as the test line. The most popular membrane used as the capture membrane is nitrocellulose, although nylon based membranes or other membranes have been used as well. This membrane is then overlapped by an absorbent pad that acts as a waste reservoir for the excess sample and sustains capillary pressure necessary for the entire sample to be drawn up through the capture membrane.

A conjugate pad is sometimes also used, on to which the conjugate (e.g., antibody coated detector particle) is dried. This conjugate pad is often integrated within the sample pad or found at the interface between the sample pad and the capture membrane whereupon the re-hydration of the conjugate occurs and begins interaction with the targeted analyte. Alternatively, the conjugate can be lyophilized and added to the sample prior to being introduced in the lateral flow test.

To run a test, a fixed volume of sample (e.g., plasma, serum, whole blood, cell lysate, urine or saliva) is added onto the sample pad whereupon certain chemical or biological treatments can occur such as the immobilization of blood cells. The sample then flows into the conjugate pad, re-hydrating the labeled antibody which begins binding to any antigen that may be present in the sample. The sample then flows into the capture membrane by capillary action where the two capture lines are located. The presence of target in the sample leads to formation of a sandwich at the test line that is visible due to the presence of the reporter antibody. Excess conjugate flows to the control line where it leads to the formation of a visible control line. The remaining sample flows into the absorption (waste) pad. For qualitative tests, the development of both lines (test and control lines) signifies a positive test, while the appearance of just the control line is a negative result.

If the control line fails to appear, the result is regarded as invalid. In semi-quantitative and quantitative lateral flow tests, the intensity of the test line is measured using an imaging device (e.g., scanner, camera) and then used to calculate the concentration of target by referring to a standard dilution curve.

A lateral flow strip upon which various reagents and/or sample are applied can be wholly or partially porous so that a mobile phase can flow on or through the strip. The strip can also be wholly or partially of a material, for example nitrocellulose, that can bind proteins. A variety of materials can be used in various portions of the strip including natural or synthetic materials including cellulosic materials such as paper, cellulose and cellulose derivatives such as cellulose acetate and nitrocellulose; fiberglass; glass fiber filter, for example WHATMAN Fusion 5 membrane (Whatman is a registered trademark of Whatman paper Limited, Kent; England); cloth, both naturally occurring and synthetic; porous gels such as silica gel, agarose, dextran and gelatin; porous fibrous matrices; starch based materials, such as cross-linked dextran chains; ceramic materials; films of polyvinyl chloride and combinations of polyvinyl chloride-silica; POREX (Porex is a registered trademark of Porex Technologies Corp., Fairburn, Ga.) and the like. Generally, the material used in the flow stream should allow liquid to flow on or through the strip. If a variety of materials are used they can be in fluid flow communication/contact or capable of being brought into fluid flow communication/contact. The strip should have sufficient inherent strength or additional strength can be provided by a supplemental support such as a plastic backing upon which porous strip components are attached.

Lateral flow tests can be used to detect one or more substances (analytes) in a fluid sample. Lateral flow strips generally include a stationary phase and a mobile phase. The stationary phase can include various reagents immobilized on the test strip. The mobile phase can include the fluid sample that flows over and/or through the test strip. The mobile phase can also include a variety of reagents. As the mobile phase flows it also can carry with it reagents that may be reconstituted from the strip. The mobile phase can also include solutions, such as dilution buffer. As an alternative to reconstitution from the strip, mobile phase reagents can be mixed with the sample prior to application of the sample to the strip.

Reaction of a substance in the mobile phase with a stationary phase reagent can generate a detectable signal. The stationary phase reagents, sometimes referred to as capture agents, can be immobilized on the strip so that they capture substances from the mobile phase. The signal can be generated by a reagent from the mobile phase, often referred to as a label, which attaches to one or more of the stationary phase reagents. Various suitable labels include chromogens, catalysts, fluorescent compounds, chemiluminescent compounds, radioactive labels, magnetic beads or magnetic particles, enzymes or substrates, vesicles containing signal producing substances, colorimetric labels, direct visual labels including colloidal metallic and metallic and non-metallic colored particles, dye particles, or organic polymer latex colored particles.

To detect the presence or absence of an analyte, test strips can be designed to provide a signal that can be observed visually, such as color changes or color differences on the test strip. The signal can also be observed, measured and/or interpreted visually. To detect the presence or absence of an analyte test strips can be designed to provide a signal that is audible. To detect the presence or absence of an analyte, test strips can be designed to provide a signal that can be observed visually and/or audibly. To detect the presence or absence of an analyte test strips can be designed to provide a signal that can be observed visually with a reader. The invention provides test strips that can be observed visually and/or with a reader and/or with an audible signal. A variety of readers are appropriate including spectrophotometers, CCD cameras, cmos cameras, reflectance readers, luminometers, fluorometers, scintillation counter, magnetic detectors and other instruments capable of reading, measuring and/or interpreting changes on a lateral flow test strip. Such instruments are described in U.S. Pat. No. 6,124,585, hereby incorporated by reference.

Compact, portable electronic devices comprising lateral flow assays have become more prevalent as technological innovations have created a wider variety of such devices for use by more and more individuals. For example, improved cellular communication services have opened up a market for greater numbers of cellular telephones, and that market is being expanded even further with the introduction of disposable cellular telephones. In addition, numerous portable electronic devices are being offered for a myriad of business, commercial and entertainment purposes.

In U.S. Pat. No. 5,965,848, the substance of which is incorporated herein by reference, there is disclosed a technology for the economical manufacture of the above-described electronic devices. The technology renders these devices easier to purchase and use, as well as convenient to vend and discard, thereby creating an even greater demand for larger numbers of such devices and a requirement for the safe and effective disposal of large numbers of expended electronic devices. The devices of the invention can be disposable electronic devices and, more specifically, disposable electronic devices constructed of deconstructable materials which render the devices more effective in accomplishing the objectives of prescribed limited service life and subsequent convenient safe disposal, as is disclosed in U.S. Pat. No. 7,148,424, incorporated by reference in its entirety.

The present invention provides for a unique and novel, inexpensive, user friendly, optionally, disposable and/or recyclable, device for an already proven technology of lateral flow with the added aspect of electronic surge to provide the sample with a rapid test result that be can heard as well as seen.

The present invention can be produced to test for a variety of biological elements including but not limited to: markers of physiological events or processes (e.g. hCG for pregnancy, LH for ovulation), of tumor development or growth (e.g. prostate specific antigen for prostate carcinoma, carcinoembryonic antigen for enteric malignancies, CA19-9 for ovarian malignancies), viral infections (e.g. HIV, HBV, HCV, herpes-type viruses, rotavirus, influenza), contaminating or infecting bacteria or fungi (e.g. *salmonella*, typhus, typhoid, MRSA), drugs (e.g. cocaine, methamphetamine, opiates), diagnostics regarding physiologically active molecules which may be altered by disease, injury, or aging (inclusive of hormones, proteins, glycoproteins, nucleotides or chromosomal fragments, etc., e.g. cortisol, insulin, leptin, adiponectin, thyroid hormone).

An example of a lateral flow test strip of the invention comprises the following components:

1. Sample pad—an absorbent pad onto which the test sample is applied.
2. Conjugate or reagent pad—this contains antibodies specific to the target analyte conjugated to colored particles (usually colloidal gold particles, or latex microspheres).
3. Reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies).
4. Wick or waste reservoir—a further absorbent pad designed to draw the sample across the reaction membrane by capillary action and collect it.

The detection of the result is made, for example, through the opto-electronic detection of the lines on the pad. The resulting electrical signal is used, for example, to activate the display of the test result as an optical and or audio message. The optical message display can be obtained by, for example, changing the color of the message thus making it different from the background as a result of the passage of an electric current. Alternatives as simple LED lighted messages or LCD displays can be used. For the audio message a transducer from electrical signals to audio signals is used as for example a piezo ceramic element. The system may be powered by a battery either independent or printed/laminated in the body of the device.

Double antibody sandwich assays—In this format, the sample migrates from the sample pad through the conjugate pad where any target analyte present will bind to the conjugate. The sample then continues to migrate across the membrane until it reaches the capture zone where the target/conjugate complex will bind to the immobilized antibodies, producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Double antibody sandwich assays are most suitable for larger analytes, such as bacterial pathogens and viruses, with multiple antigenic sites. Competitive assays are primarily used for testing small molecules and differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone, an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. Competitive assays are most suitable for testing for small molecules, such as mycotoxins, unable to bind to more than one antibody simultaneously. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed. Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory. However, their sensitivity is limited without additional concentration or culture procedures.

Quantitative tests—While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan™ lateral flow reader for use with its range of Reveal® assay kits and Charm Sciences also supplies a reader for its Rosa® range of mycotoxin test strips. More sophisticated techniques, such as fluorescent dye labeled conjugates, have also been developed to improve the quantitative potential of lateral flow assays. Applications in the 20 years since the first lateral flow test was launched have expanded to include a huge range of different tests that have been developed based on the same technology. The first commercially available kits were aimed at the clinical diagnostics field, but there are now products with applications in almost every branch of microbiology.

Clinical microbiology—lateral flow tests have been developed for bacterial pathogens, respiratory and enteric viruses, intestinal parasites and bacterial toxins. Many of the lateral flow immunoassay products designed for the clinical sector are intended to be used at the point-of-care for direct testing of fecal, blood and urine samples and nose and throat swabs, where the simple operation and speed of the tests is key to their use outside of the laboratory. However, the same test strips may also be useful as a quick confirmatory test following laboratory culture of clinical samples.

Food and agricultural microbiology—test strips are available for food borne bacterial pathogens, bacterial and fungal toxins. In the food microbiology sector, the main applications are more likely to be in the laboratory, although there are field test kits for mycotoxins in grain samples. Testing for food borne bacterial pathogens generally involves at least one enrichment stage before the assay strip is used to confirm the presence or absence of the pathogen. Some manufacturers, such as Dupont®, have developed enrichment media and methods specifically designed for use with lateral flow test strips. Test strips may also be useful for rapid confirmation of the identity of bacterial isolates from conventional microbiological testing.

Electronic Surge

The device of the invention may comprise, for example, temperature control elements, particularly heating elements, including, for example, resistive heaters. Cooling elements may include heat sinks, radiative heat fins and other components to facilitate radiative heat loss. Thermal devices can be applied to the device as a whole, or in specific areas of the device. The temperature of any particular area on the disk may be monitored by, for example, resistive temperature devices (RTD), thermistors, liquid crystal birefringence sensors infrared interrogation using IR-specific detectors. Temperature at any particular region of the device can be regulated by feedback control systems. A micro-scale thermo-control system can be fabricated directly in the device.

The heating is provided by an electrical heating element which is commanded and controlled electronically using either a digital logic or an analog control loop, or a combination of both. The controlling circuitry allows the heating of the sample at a certain temperature for a given period of time. The heating element consists of a material that heats during the passage of currents and can be implemented as a wire or a thick film element or a thin film element. The layout of the heating element is function of the exact implementation of the active part of the "pad".

The device of the invention may provide, for example, electronic surge to a sample via a circuit. The device of the invention may provide, for example, electronic surge to a sample via a battery driven circuit. The invention provides that the speed of the result may be increased by application of heat to the sample. The invention provides that the electric current source may be connected to a conductive material for inducing resistive heating therein, thereby heating the sample.

Digital Reader

The invention provides for a digital reader that provides the user with both, for example, a visual and/or audio result. An example of this would be the determination of, for example, pregnancy. The pregnancy device would include conventional sensors to provide the user with a color band that appears or is absent when a specific antigen is present in a human fluid such as detecting chorionic gonadotropin (hCG) in urine for pregnancy testing. The speed of result can be increased with the electronic surge generated by a battery driven circuit to the sample. The result can then be visually read and/or revealed through audio means whereby the unit announces "Congratulations You Are Pregnant" or "I'm sorry you are not pregnant, better luck next time". A further example is a digital reader that provides the user with both a visual and/or audio result of the determination of, for example, cortisol levels, wherein the result can then be visually read and/or revealed through audio means. The result can also be coupled with a fluorescent dye conjugate and read on a fluorescence reader. A device coupling lateral flow with the sensitivity of fluorescence would exhibit increased sensitivity.

Display

The device of the invention can comprise a display device which may be, for example, visual, audio, or both visual and audio. The display device can be any type of generally low powered displays capable of producing a representation of the test result computed in the device based on the sample read by the device. In various embodiments, the display device is, for example, an LED display, a liquid crystal display, or other similar display types. The display device might be internal or external.

Electronic display devices are well known in the art and are available in a variety of technologies such as vacuum fluorescent, liquid crystal, or Light Emitting Diode (LED). The user can read alphanumeric data as it is displayed on the electronic display device. Audio output devices can also include for example, a synthetic speech output device, electronic sound file playback system (WAV, MP3, etc.), or voice synthesizer. The audio output device might be internal or external.

The device of the invention can comprise a display device, such as a touch screen monitor or touch screen LCD panel, and/or audio input device, for touch and/or voice control.

Diagnostic System

A diagnostic system in kit form of the present invention may include, for example, a device of the invention for detecting the presence of a biological substance in a test sample, As used herein, the term "package" refers to a solid matrix or material such as glass, plastic, paper, foil and the like capable of holding within fixed limits, for example, a device of the invention.

A diagnostic system in kit form of the present invention may include, for example, instructions for use. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

Signal Generating Agent

The signal generating agent can comprise a labeling means which can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium or $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

Specific Binding Agent

The diagnostic systems can also include a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably the specific binding agent binds the reagent species when that species is present as part of a complex.

A "specific binding agent," as used herein, may be a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding agents, for example, an analyte-analog. Immunoreactive specific binding agents include antigens, antigen fragments, antibodies and antibody fragments, both monoclonal and polyclonal and complexes thereof, including those formed by recombinant DNA molecules.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

Thus, for example, a polypeptide, antibody molecule composition or monoclonal antibody molecule composition of the present invention can be affixed to a solid matrix to form a solid support that comprises a package in the subject diagnostic systems. The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of, for example, cortisol. Such a system comprises, in kit form, a package containing an antibody to, for example, cortisol.

Sample

"Sample" refers to, for example, essentially any source from which materials of interest to be analyzed (e.g., ligands and antiligands, such as antibodies and antigens, and nucleic acids and their complements) can be obtained. A sample may be acquired from essentially any organism, including animals and plants, as well as cell cultures, recombinant cells and cell components. Samples can be from a biological tissue, fluid or specimen and may be obtained from a diseased or healthy organism. Samples may include, but are not limited to, saliva, sputum, amniotic fluid, blood, blood cells (e.g., white cells), urine, semen, peritoneal fluid, pleural fluid, tissue or fine needle biopsy samples, and tissue homogenates. Samples may also include sections of tissues such as frozen sections taken for histological purposes. Typically, samples are taken from a human. However, samples can be obtained from other mammals also, including by way of example and not limitation, dogs, cats, sheep, cattle, and pigs. Samples can be obtained from agricultural sources. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

Biological samples can be derived from patients using well known techniques such as venipuncture, lumbar puncture, fluid sample such as saliva or urine, or tissue biopsy and the like. When the biological material is derived from non-humans, such as commercially relevant livestock, blood and tissue samples are conveniently obtained from livestock processing plants. Similarly, plant material used in the invention may be conveniently derived from agriculture or horticultural sources, and other sources of natural products. Alternatively, a biological sample may be obtained from a cell or blood bank where tissue and/or blood are stored, or from an in vitro source, such as a culture of cells. Techniques for establishing a culture of cells for use as a source for biological materials are well known to those of skill in the art.

In one embodiment, the sample is selected from or is derived from the group comprising: agricultural product, microbial product, and biological product.

In another embodiment, the agricultural product is selected from the group comprising a seed, grain or plant extract.

In another embodiment, the sample contains particulate materials selected from the group comprising grain extract, cell extract and microbial extract.

Although the above described example relates to the antigens relating to disease, the immunoassay apparatus could be used, for example, as an allergy test kit, as a test kit for drugs of abuse or for analyzing non-human derived samples, e.g., bovine, porcine, veterinary tests, and tests in agriculture such as grain quality evaluation, etc.

Specific reagents used in the assay device will be selected to ensure that the particular target analyte is detected, as is well known in the art. The target analyte may be any analyte, for example, a chemical reagent which may be organic or inorganic, and which optionally comprises a hapten, a protein, a polypeptide, a microorganism or a nucleic acid sequence.

Analytes

"Analyte," as used herein, is the substance to be detected which may be present in the test sample, including, biological molecules of interest, small molecules, pathogens, and the like. The analyte can include a protein, a polypeptide, an amino acid, a nucleotide target and the like. The analyte can be soluble in a body fluid such as blood, blood plasma or serum, urine or the like. The analyte can be in a tissue, either on a cell surface or within a cell. The analyte can be on or in a cell dispersed in a body fluid such as blood, urine, breast aspirate, or obtained as a biopsy sample. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; ibuprofen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti- HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

In some embodiments, the analyte to be detected is a protein, peptide, small molecule; antibody, nucleic acid, virus, virus particle, drug, drug metabolite or small molecule. Specific examples include, but are not limited to, human chorionic gonadotrophin, luteinizing hormone, estrone-3-glucoronide, pregnanediol 3-glucoronide, insulin, glucagon, relaxin, thyrotropin, somatotropin, gonadotropin, follicle-stimulating hormone, gastrin, bradykinin, vasopressin, polysaccharides, estrone, estradiol, cortisol, testosterone, progesterone, chenodeoxycholic acid, digoxin, cholic acid, digitoxin, deoxycholic acid, lithocholic acids, vitamins, thyroxine, triiodothyronine, histamine, serotorin, prostaglandin, drugs, drug metabolites, ferritin or CEA.

In some embodiments, immunoassays utilize antibodies to a purified protein (e.g., analyte). Such antibodies may be polyclonal or monoclonal, chimeric, humanized, single chain or Fab fragments, which may be labeled or unlabeled, all of which may be produced by using well known procedures and standard laboratory practices. See, e.g., Burns, ed., Immunochemical Protocols, 3rd ed., Humana Press (2005); Harlow and Lane, Antibodies: A Laboratory Manual, Cold Spring Harbor Laboratory (1988); Kozbor et al., Immunology Today 4: 72 (1983); Kohler and Milstein, Nature 256: 495 (1975). In some embodiments, commercially available antibodies are utilized.

In particular, the analyte may be a hormone such as a fertility hormone like progesterone or a stress hormone such as cortisol. However, there is a wide range of applications of these types of tests across the entire field of diagnostics and analysis. Detection of marker proteins or hormones can be diagnostic of certain disease conditions in humans or animals, and the presence of drugs or drug residues may also be required to be detected, for example, in animal husbandry, forensic medicine or in the testing for banned or prohibited drug substances.

Alternatively, the analyte is a chemical reagent, for instance a small molecule, which suitably comprises a hapten. Small molecules will generally comprise a single recognizable binding site. Typically they will have a molecular weight of less than 1 kDa.

The method of the invention may be particularly useful in the detection of agrochemicals, both active agrochemicals and as residues.

For instance, the method described above can be utilized in agriculture to detect particular pests or pathogens on crop plants, such as fungal antigens or viral infections. They may also be utilized to detect pesticide residues on crops. They may also be utilized to detect genetically modified organisms (GMO) or genetically modified food.

The applicants have found however that analytical techniques of this type can be applied more widely and in particular can be used to assist in the growing process.

Thus, in a particular embodiment, there is provided a method for detecting the presence of amount of an active agrochemical contained within plant tissue, said method comprising extracting said plant tissue into a solvent in which said active agrochemical is soluble, and detecting active agrochemical within said sample using a method as described above.

As used herein the term "agrochemical" refers to any chemical reagent which has a desirable effect on crops. They may be organic or inorganic molecules, as well as proteins, polypeptides and peptides. Most typically, the agrochemical will comprise small organic molecules. Agrochemicals may comprise herbicides, fungicides, insecticides and plant growth regulators, which may be applied to growing plants or as seed treatments. In some cases, the plants themselves may be genetically engineered to express the agrochemical, for instance, an insecticides based upon *Bacillus thurigiensis* derived proteins (Bt).

In accordance with a particular embodiment of the invention, only active agrochemical is detected and not any residues. This may be achieved by conducting an assay that tests for activity, but is more conveniently carried out by detecting the active chemical itself. Most agrochemical compounds, or indeed any biologically active material, such as therapeutic or prophylactic compounds, may comprise active chemical groups or elements that are "used up" when the biological activity is initiated. For example, agrochemicals may contain a "warhead" which may be broken down after use, for example by metabolism within a plant, or by degradation as a result of exposure to light or to conditions found in the soil or the like.

The mechanism by which many biologically active materials such as agrochemicals are degraded is frequently well understood, and so therefore, it is generally clear what particular chemical elements within the molecule is required for the biological activity, and which elements are degraded once the agrochemical has been used. By assaying for one of these elements, the presence of active molecules only will be detected.

By detecting the biologically active material such as the active agrochemical in a semi-quantitative manner as described above, it is possible to determine whether the amount of the biologically active material within a particular sample is of a level which is sufficient to provide the desired activity. This means that the results can be used to determine whether further application of the biologically active material agrochemical, is required in order to achieve the desired result, which in the case for example of an agrochemical is for the plant to benefit from the effect thereof.

The method is suitably applied to any convenient sample of plant tissue, and this will vary depending upon the nature of the crop and the agrochemical being treated. In many cases however, suitable plant tissue is leaf tissue. It may be desirable, for example in the case of insecticides which are active against biting pests, to determine how much active material remains on the surface of the leaf.

Generally however, where the agrochemical has a systemic effect on the plant, it will be necessary to remove any material which remains on the surface of the leaf before analyzing the tissue. This can be easily done by first subjecting the leaf tissue to a washing step so as to remove agrochemical from the surface thereof. Thereafter, a sample can be generated for example by macerating or otherwise disrupting the leaf structure, and detecting material in the sample obtained. In this way, only agrochemical which has penetrated the leaf is detected.

A particularly convenient way of obtaining such a sample is to add a sample of the leaf to a container, for example a bottle, which contains a solvent, and a solid such as ball-bearings, and shaking the container to allow the solid to disrupt the leaf, allowing agrochemical to be dissolved into the solvent. This then forms the sample for analysis.

Alternatively, the plant tissue is root tissue. This may also be suitable in the case of systemically acting agrochemicals, as well as seed treatments. It may be particularly suitable for testing for agrochemicals which are intended to protect the roots from attack, for example, for nematicides or fungicides.

When the biologically active material is other than an agrochemical, suitable sample preparation methods will be those generally known in the art. For instance, biological fluids such as urine, plasma and milk may require little preparation, whereas other samples may be prepared by applying conventional extraction techniques.

Where the assay utilizes a labelled binding partner for the analyte and the analyte is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or Van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid.

Where the analyte is or comprises a hapten or a protein antigen, the binding partner may comprise an antibody or a binding fragment thereof, which may be monoclonal, polyclonal or recombinant, but preferably is monoclonal. Where the analyte is a hormone or enzyme, the labelled binding partner may comprise a labelled receptor for the analyte. However, where the analyte is itself an immunoglobulin, and in particular, an antibody, the labelled binding partner may also comprise for instance, an antigen or recombinant antigen, as well as anti-antibody immunoglobulin such as antisera.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

For example, where the analyte is a biologically active material, specific reagents used in the assay device will be selected so as to ensure that the particular target biologically active material is detected as is well known in the art. The biologically active material may be any active chemical such as an agrochemical, for example a chemical reagent which may be organic or inorganic, and which optionally comprises a hapten, a protein, a polypeptide, a microorganism or a nucleic acid sequence. Most preferably the biologically active material is a chemical reagent, for instance a small molecule, which suitably comprises a hapten. Small molecules will generally have a single antibody binding site. Typically they will have a molecular weight of less that 1 kDa.

For instance, where the assay utilizes a labelled binding partner for the active agrochemical and the active agrochemical is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid. Conversely, the binding partner may comprise the acid part of the reactive pair.

Where the analyte is a biologically active material, such as an active agrochemical, or comprises a hapten or a protein antigen, the binding partner may comprise an antibody or a binding partner therefore, which may be monoclonal, polyclonal or recombinant, but preferably is monoclonal.

Where the analyte is a biologically active material such as an active insecticide, for instance, an organophosphate pesticide, which has activity as a nerve agent, the binding partner for it may comprise a suitable receptor or binding fragment thereof. Particular receptors may comprise acetyl cholinesterase receptors.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

The hapten used will suitably comprise the active chemical group, for instance an agrochemical or a fragment or functional group or "warhead" which is present in the active form of the agrochemical but not in spent material such as material which has been metabolized, for example by the plant and is, as a result, no longer active.

Suitable examples of binding agents which may be used to detect agrochemicals and their preparation are described for example in WO01/42787, which describes antibodies for neonicotinyl insecticides, EP-A-1043336, which describes antibodies which are specific for imidazolinone herbicides, J. K. Lee et al., J. Agric. Food Chem. 2003, 51, 3695-3703 which describes antibodies for organophosphorus insectides, in particular acetphate, J. F. Lawrence et al. J. Chromatography (1996) 732, 277-281 which describes antibodies to phenylurea herbicides, and J. F. Lawrence et al. J. Chromatography (1996) 752, 147-154 which describes antibodies to triazine herbicides.

Where these references describe polyclonal antibodies, for the purposes of the present invention, these are preferably used to generate monoclonal antibodies using conventional techniques. Where a particulate label is used, the binding partner is suitably coated all over the particle, which maximizes the chances that the particle will take part in any binding action possible, either with the analyte or with the immobilized analogue of the analyte in the detection zone. Similarly, where the assay utilizes the analyte or an analogue of the analyte, this also may be coated onto a particulate label for maximum sensitivity. The amount of reagent immobilized in the detection zone is controlled so as to generate the desired signal.

The analogue of the target analyte used, in particular as the immobilized element in the detection zone, could be a fungal extract containing the target analyte where this is of fungal origin, or a protein-hapten conjugate where the hapten is the analyte or a derivative of the analyte.

Patient

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

The invention will be illustrated in more detail with reference to the following Examples, but it should be understood that the present invention is not deemed to be limited thereto.

EXAMPLES

Example 1

Ampicillin

Colloidal Gold—One milliliter of 1% HAuC14 solution was added to 97.5 ml of deionized water and it was boiled. When mixing, 1.5 ml of 1% sodium citrate was added. The mixture was boiled for 25 min, then it was cooled and stored at 4-6° C.

Synthesis of CGantibodies conjugates. For this purpose, 1.0 ml of CG solution (D520=1.0) was added to 0.1 ml of aqueous solution of antibodies (concentration varied from 5 to 250 µg/ml) and it was mixed and incubated for 10 min at room temperature. Then, 0.1 ml of 10% NaCl was added into each probe and it was mixed. D580 was measured in 10 min. Before conjugation with CG, the antibodies were dialyzed against 1,000 fold volume of 10 mM trisHCl buffer (pH 8.5) for 2 h at 4° C. To CG solution, 0.2 M K2CO3 was added (D520=1.0) until pH 8.5, and a solution of antibodies at a certain concentration was spiked. The mixture was incubated for 30 min at room temperature and with mixing; following this, BSA was carried up to a final concentration of 0.25%. CG particles with antibodies immobilized on them were separated from noninteracting antibodies by centrifugation at 8000 g for 30 min. After removal of supernatant, the precipitate was resuspended in PBS containing 0.25% BSA. If long term storage was necessary, NaN3 was added to the received product up to final concentration of 0.02%.

Preparation of the immunochromatographic test. Application of reagents on membrane in the test system was conducted using an automatic dispenser. The colloidal gold-antibody conjugate was applied on a pad at a dilution corresponding to D520=2.0 (32 µl for 1 cm of substrate width). For formation of analytic zone, the penicillin-BSA conjugate (0.2 mg/ml in 0.2M carbonate buffer, pH 9.6) was used; for formation of control zone, goat antimouse IgG antibodies (GAMI, 0.25 mg/ml in PBS) were used. Both solutions were stabilized and applied in 2.0 µl for 1 cm of working membrane width. The resulting membranes and pads were air dried at 20-22° C. no less than 20 h. Multimembrane composite was obtained from which strips with the width of 3.5 mm were obtained. (N. A. Byzova, E. A. Zvereva, A. V. Zherdev, and B. B. Dzantiev. Immunochromatographic Technique for Express Determination of Ampicillin in Milk and Dairy Products. Prikladnaya Biokhimiya i Mikrobiologiya, 2011, Vol. 47, No. 6, pp. 685-693.)

Example 2

Pregnancy Test

Each test strip comprises a plastic backing (6 cm×5 mm) with adhesive on both sides. The plastic backing is between about 2 mil and about 20 mil in thickness. A test line and a control line are prepared on a nitrocellulose membrane (Millipore HF09004) by spraying with a pump dispensing system (Kinematic Automation). The test line comprises a vertical line of a antibody to human chorionic gonadotropin (hCG), preferably a monoclonal antibody. Antibodies to hCG are widely available commercially, for example from Research Diagnostics Inc. (RDI-CBL74; New Jersey, USA), Charles River Labs and other sources or may be prepared using standard procedures. A total amount of from about 0.2 to about 1 ug of antibody is applied to the test area in a vertical line. The control line comprises a vertical line of Protein A. A total amount of Protein A sufficient to produce a visible signal upon conjugate binding is applied to the control line, typically about 0.25 ug. For each test strip, the appropriate nitrocellulose membrane is cut to a size of about 2.5 cm×5 mm and attached to the plastic backing. A second antibody to hCG is attached to colloidal gold for 30 the conjugate for the test. Colloidal gold-hCG antibody conjugates are available commercial, for example from Research Diagnostics Inc. Alternatively hCG antibody conjugates can be prepared using well known methods (See, e.g., U.S. Pat. No. 6,485,982, incorporated herein by reference). The conjugate is diluted in conjugate buffer to a concentration of approximately 3OD/m!. The conjugate buffer preferably comprises 0.25% HEPES, 0.85% sodium chloride, 0.1% sodium azide, 0.1% EDTA, 0.1% casein, 1% bovine serum albumin, 1% mannitol, 5% sucrose, and 0.1% Triton XIOO. The buffer is adjusted to a pH of 7.2. Conjugate is applied to a glass fiber conjugate pad (Millipore GFCP203000), which is dried and cut into 5 mm×5 mm strips. A Whatman GF/DVA glass paper buffer pad (2 cm×5 mm) is attached to the dried conjugate pad of each test strip to serve as the buffer pad. An absorbent pad (2 cm×5 mm) made of S&S 900 paper is attached to the end of the nitrocellulose membrane closest to the control area and a further absorbent paper (2.5 cm×5 mm; 50 S&S 470) is attached to the absorbent pad. The absorbent paper is in turn in contact with a desiccant tablet (e.g., TriSorb, Sud-Chemie), that is able to absorb a significant portion of the sample volume and thus draw sample and analyte across the test area. Methylene blue, or another indicator, is deposited on one of the absorbent pad or absorbent paper, downstream of the test area. The movement of this volume indicator is a signal that sufficient sample has contacted the test area to allow for an accurate test. See U.S. Pat. No. 7,393,697.

Example 3

Immunochromatography Assay for Detection of Aflatoxin B1

Materials—Chloroauric acid (HAuCl4-3H2O) and sodium citrate were used without further purification. Deionized and distilled water was. Aflatoxin B1 (AFB1), bovine serum albumin (BSA) and horseradish peroxidase (HRP), goat anti-rabbit antibody were obtained from Sigma (Sigma, St. Louis, Mo., USA). AFB1-BSA and AFB1-HRP were produced. Polyclonal antibody to AFB1 was generated in rabbits by immunizing the animals with AFB1-BSA. High-flow nitrocellulose membrane, glass fiber and absorption pad were obtained from Schleicher and Schuell (Dassel, Germany). Phosphate-buffered saline (PBS, pH 7.4, 0.01 M in 0.85% NaCl) was prepared. All other chemicals used in the present study were either analytical pure or with highest quality.

Synthesis and characterization of colloidal gold—An aqueous solution of chloroauric acid (50 ml of 0.01% [w/v] HAuCl4d 3H2O) was heated to boiling. Sodium citrate solution (2 ml of 1% [w/v]) was added while stirring rapidly to yield colloidal gold particles according to Frens, with modification. Chloroauric acid solution was brought to boiling in an Erlenmeyer flask with a reflux condenser on a magnetic stirrer with electric heating, then 2.0 ml of aqueous 1% sodium citrate solution was added to the flask. The original boiling time was 2 min, reaction time was 5-6 min, and the mixing speed was 1000 rpm. Solutions used in making colloidal gold were dialyzed against water to remove some electrolyte ions, which can react with atomic gold.

2.3. Formation of conjugates Polyclonal antibody (0.78 mg) prepared in pH 7.4 phosphate-buffered solution (0.01 M) was added drop-wise to 20 ml of colloidal gold solution ([Au] =2.4×104 mol/l) while stirring to yield a final antibody concentration of 0.039 mg/ml in the colloidal solution. The pH of the colloidal gold solution was adjusted to pH 7.4 by addition of dilute 0.01 M Na2CO3 before adding the antibody. This was done inasmuch as the optimum stability of the conjugates is at pH 7.4, and the least content of antibody was 0.030 mg/ml of gold solution. The solution was stored for a period of 2 h at 4 8 C and centrifuged to remove unconjugated antibody from the solution. Centrifugation was done at 10000 rpm in a DuPont Sorvall RC-B123 super speed centrifuge cooled to 4 8 C. The pellet obtained was dispersed in buffer solution, centrifuged once again to remove free unconjugated antibody (if any) and redispersed in 4 ml of pH 7.4 PBS and stored at 4 8 C for further experiments. In the final antibody-gold conjugate solution, colloidal gold concentration in the final antibody-gold [Au] conjugate solution was about 1.0103 mol/l, and antibody concentration as calculated to be 0.11 mg/ml.

Preparation of immunochromatography test strip. Construction of lateral flow test strip. Gold-labeled antibody probe (without dilution) was jetted onto the glass fiber and dried at room temperature. Goat antirabbit anti-S antibody (500 g/ml) and AFB-BSA antigen (500 g/ml) in PBS were jet-positioned onto a nitrocellulose membrane as two discrete zones, one for control and the other for test. The remaining active sites on the membrane were blocked by incubation with 1% BSA in PBS (1 ml/cm membrane) for 30 min at room temperature. The membrane was washed once with PBS and twice with distilled water and then dried. The conjugate pad was prepared by adding the colloidal gold probe particles coated with anti-AFB polyclonal antibody onto a glass fiber at the site of 15 mm from the bottom end and then dried. The jetted nitrocellulose, absorption pad and conjugated pad components were dried and laminated. The laminated sheet was then cut into individual strips (3.5 mm/strip), using a strip cutter model CM4000 supplied by Biodot. (Sun Xiulan, Zhao Xiaolian, Tang Jian, Jun Zhou, F. S. Chu. Preparation of gold-labeled antibody probe and its use in immunochromatography assay for detection of aflatoxin B1. International Journal of Food Microbiology 99 (2005) 185-194.)

While the invention has been described in detail and with reference to specific examples thereof, it will be apparent to one skilled in the art that various changes and modifications can be made therein without departing from the spirit and scope thereof.

What is claimed is:

1. A lateral flow device for qualitative or quantitative analysis of a target analyte in a sample, comprising:
   a disposable electronic device having a body constructed of juxtaposed lengths of an elongate, folded, ribbon-like substrate of dielectric material secured together to establish a multiple-layered structure, and circuitry formed on the substrate, wherein at least a portion of the circuitry is constructed of a deconstructable material which deconstructs to render the device inoperative in response to reaching a predetermined accumulated amount of time during which the circuitry is operated;
   wherein the device comprises components disposed on the ribbon-like substrate in the following order:
   an absorbent sample pad onto which the sample is applied;
   a conjugate or agent pad comprising at least one specific binding agent specific to the target analyte, and optionally conjugated to a signal-generating agent;
   a reaction membrane onto which at least one capture agent is immobilized in a line across the membrane as a capture zone or test line, further optionally comprising a control zone, containing a binding agent specific for the capture agent; and
   a wick or waste reservoir, which draws the sample across the reaction membrane and collects it; and
   wherein the ribbon-like substrate comprises:
   at least one circuit to provide an electronic surge to the sample and an electric current source, wherein the electric current source is connected to the circuit for inducing controlled resistive heating therein to heat the sample, wherein the electric current source is a battery; and
   a means to indicate the results, wherein the means to indicate the result is selected from the group consisting of visual means, audio means, and combinations thereof; and
   further wherein the speed of the result is increased by application of heat to the sample.

2. The device of claim 1, wherein the results of the analysis are increased with the electronic surge generated by a battery driven circuit to the sample to provide heat.

3. The device of claim 1 wherein the substrate comprises paper.

4. A method for the manufacture of the lateral flow device of claim 1, the method comprising the following steps:
   providing a disposable electronic device having a body constructed of juxtaposed lengths of an elongate, folded, ribbon-like substrate of dielectric material secured together to establish a multiple-layered structure, and circuitry formed on the substrate, wherein at least a portion of the circuitry is constructed of a deconstructable material which deconstructs to render the device inoperative in response to reaching a predetermined accumulated amount of time during which the circuitry is operated;
   wherein the device comprises components disposed on the ribbon-like substrate in the following order:
   an absorbent sample pad onto which the sample is applied;
   a conjugate or agent pad comprising at least one specific binding agent specific to the target analyte, and optionally conjugated to a signal-generating agent;

a reaction membrane onto which at least one capture agent is immobilized in a line across the membrane as a capture zone or test line, further optionally comprising a control zone, containing a binding agent specific for the capture agent; and a wick or waste reservoir, which draws the sample across the reaction membrane and collects it;

wherein the ribbon-like substrate comprises:

at least one circuit to provide an electronic surge to the sample and an electric current source, wherein the electric current source is connected to the circuit for inducing controlled resistive heating therein to heat the sample, wherein the electric current source is a battery; and a means to indicate the results, wherein the means to indicate the result is selected from the group consisting of visual means, audio means, and combinations thereof; and further wherein the speed of the result is increased by application of heat to the sample, and assembling these components into a lateral flow device.

5. A method of detection of analyte in a sample, comprising application of a biological sample to the device of claim 1.

* * * * *